United States Patent
Park et al.

(10) Patent No.: US 11,534,261 B2
(45) Date of Patent: Dec. 27, 2022

(54) LASER PROJECTION APPARATUS, CONTROL METHOD THEREOF, AND LASER GUIDANCE SYSTEM INCLUDING THE APPARATUS

(71) Applicant: KYUNGPOOK NATIONAL UNIVERSITY INDUSTRY-ACADEMIC COOPERATION FOUNDATION, Daegu (KR)

(72) Inventors: Ilhyung Park, Daegu (KR); Chulwoo Park, Daegu (KR); Hyunwoo Lee, Daegu (KR); Sanghyun Joung, Daegu (KR); Youngkyun Park, Daegu (KR); Jihun Yu, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 386 days.

(21) Appl. No.: 16/956,847

(22) PCT Filed: Dec. 20, 2018

(86) PCT No.: PCT/KR2018/016393
§ 371 (c)(1),
(2) Date: Jun. 22, 2020

(87) PCT Pub. No.: WO2019/132427
PCT Pub. Date: Jul. 4, 2019

(65) Prior Publication Data
US 2020/0322582 A1     Oct. 8, 2020

(30) Foreign Application Priority Data
Dec. 27, 2017 (KR) .................. 10-2017-0180581

(51) Int. Cl.
*G06T 7/00* (2017.01)
*A61B 6/00* (2006.01)
(Continued)

(52) U.S. Cl.
CPC .............. *A61B 90/36* (2016.02); *G06F 3/042* (2013.01); *G06K 9/6201* (2013.01);
(Continued)

(58) Field of Classification Search
CPC .............. G06T 7/00; A61B 6/00; A61B 90/00
See application file for complete search history.

(56) References Cited

U.S. PATENT DOCUMENTS 6,364,526 B2 * 4/2002 Ivan ..................... A61B 6/4441
378/198
7,853,311 B1 * 12/2010 Webb .................. A61B 6/4423
128/849
(Continued)

FOREIGN PATENT DOCUMENTS

| JP | 3792257 B2 | 7/2006 |
|----|-----------|--------|
| JP | 4110457 B2 | 7/2008 |

(Continued)

OTHER PUBLICATIONS

_ C-arm fluoroscopy guided progressive cut refinement strategy; Yao—2000. (Year: 2000).*

(Continued)

*Primary Examiner* — Luis Perez-Fuentes
(74) *Attorney, Agent, or Firm* — Novick, Kim & Lee PLLC; Jae Youn Kim

(57) ABSTRACT

Provided is a laser projection apparatus, a control method thereof, and a laser guidance system including the laser projection apparatus. The laser projection apparatus for projecting planned operation information of an insertion location and an insertion angle on a C-arm image photo- (Continued)

graphed using a C-arm fluoroscopy device directly onto an affected part includes a line laser module configured to generate a line laser and to form a plane by rotating around an origin, a matching unit configured to calculate a coordinate representing the insertion location in a C-arm coordinate system based on C-arm fluoroscopy, calculate an insertional vector according to the coordinate representing the insertion location and the insertion angle, and calculate a vector perpendicular to the plane formed by the line laser in the C-arm coordinate system according to the insertional vector, and a control unit configured to control the line laser module based on the vector perpendicular to the plane.

20 Claims, 9 Drawing Sheets

(51) Int. Cl.
*A61B 90/00* (2016.01)
*G06F 3/042* (2006.01)
*G06K 9/62* (2022.01)
*A61B 34/10* (2016.01)

(52) U.S. Cl.
CPC ... *A61B 2034/107* (2016.02); *A61B 2090/366* (2016.02); *A61B 2090/3764* (2016.02)

(56) References Cited

U.S. PATENT DOCUMENTS

| | | | | |
|---|---|---|---|---|
| 8,118,818 B2* | 2/2012 | Zheng | ............... | A61B 34/20 |
| | | | | 606/130 |
| 9,008,279 B2* | 4/2015 | Grzeda | ............... | A61B 6/547 |
| | | | | 378/162 |
| 11,065,063 B2* | 7/2021 | Tatsui | ............... | A61B 18/24 |
| 11,191,592 B2* | 12/2021 | Gorek | ............... | A61F 2/4657 |
| 2020/0009404 A1* | 1/2020 | Fujii | ............... | A61N 5/1037 |

FOREIGN PATENT DOCUMENTS

| | | |
|---|---|---|
| JP | 5248474 B2 | 7/2013 |
| JP | 2014-533168 A | 12/2014 |
| KR | 10-0731052 B1 | 6/2007 |
| KR | 10-1152177 B1 | 6/2012 |
| KR | 10-1650620 B1 | 8/2016 |
| KR | 10-2017-0125023 A | 11/2017 |

OTHER PUBLICATIONS

_ C-arm tracking and reconstruction without an external tracker; Jain—2006. (Year: 2006).*
_ Intra-operative 3D guidance using Non-isocentric C-arm; Jain—2007. (Year: 2007).*
_ C-arm fluoroscopy in orthopedic surgical practice; Dec. 2018. (Year: 2018).*

* cited by examiner

LASER PROJECTION APPARATUS, CONTROL METHOD THEREOF, AND LASER GUIDANCE SYSTEM INCLUDING THE APPARATUS

TECHNICAL FIELD

This disclosure relates to a laser projection apparatus, a control method thereof, and a laser guidance system including the laser projection apparatus, and more particularly, to a laser projection apparatus for projecting an insertion location and posture of a fixing screw, a drill, a guide, or the like onto an affected part during a surgical operation, a control method thereof, and a laser guidance system including the laser projection apparatus.

BACKGROUND ART

Though a surgical operation using an image device is planned, it is difficult to proceed with the operation as planned at an actual operation site. As a simple example, in the case of the osteotomy, if the osteotomy is planned to take place at 5 cm lower than the knee joint, it is necessary to perform incision by 5 cm using a ruler at the actual knee, which is exposed by incision of the skin, and then perform a surgical operation accordingly. However, there are many differences between the real surgery and the plan depending on the position and angle of the ruler.

In particular, when marking a surgical perforation point using a writing instrument based on the manual work of a medical staff, especially when a perforation is necessary, the medical staff must rely on a 2D image of a fluoroscopy device (or, a C-armed fluoroscopy). However, the fluoroscopy device does not provide any important information as to whether to enter the affected part at the skin of the patient perpendicularly or at a slanted angle. Therefore, the surgical operation has to be inevitably performed depending on the surgical experience or intuition of the medical staff.

Moreover, the results of the surgery in the operating room depend largely on the surgical experience of the medical staff performing the surgery or the medical interpretation ability on the affected part image information. Thus, in the case of a medical staff with insufficient surgical experience, a continuous preparation training for accurate surgical performance is required for a considerable period of time, and as a result, there is a problem of increased expenditure of human labor and material expenses for the required training.

Accordingly, guidance for accurately performing a planned surgery is required. Conventionally, an image of a patient is acquired by using equipment such as a computed tomography (CT) or a magnetic resonance (MR) device, and a marker or the like is installed in a certain place, such as the leg of a patient, in the operating room (the marker is an auxiliary tool for aligning coordinates), and the image taken through MRI in the operating room must be matched (coordinate matching) using the corresponding marker.

Therefore, since two processes of displaying the marker on the human body of the patient and matching the marker with the image are required, there is a problem in that the surgical process is complicated and real-time guidance is not provided. In addition, since the matching of the marker and the image is not precise, there is a risk of adversely affecting the surgical operation that demands a high degree of accuracy.

In particular, in the orthopedic surgery, a mobile C-arm fluoroscopy (hereinafter, referred to as a C-arm) is frequently used to check the condition of bone, establish a surgical plan such as osteotomy and alteration correction, and then perform the surgery. To this end, a k-wire (stainless-steel wire) is placed on the affected part, a C-arm image is taken, and a location between the bone and the k-wire is measured to make a surgical plan.

The laser projection apparatus is a device that displays lines planned in the C-arm image directly on the affected part, and it is essential to accurately match the positions of the C-arm and a laser target device required to use the apparatus.

DISCLOSURE

Technical Problem

According to an aspect of the present disclosure, there is provided a laser projection apparatus which matches a position with a C-arm in order to project a line laser to a position according to operation information planned on a C-arm image.

According to another aspect of the present disclosure, there is provided a control method of the laser projection apparatus for generating a line laser to display the operation information planned on the C-arm image to the affected part.

According to another aspect of the present disclosure, there is provided a laser guidance system for displaying operation information of an insertion location and an insertion angle planned on the C-arm image directly to the affected part as an intersection point of two-line lasers.

Technical Solution

A laser projection apparatus according to an embodiment of the present disclosure in order to solve the above object, which projects operation information of an insertion location and an insertion angle planned on a C-arm image photographed using a C-arm fluoroscopy (hereinafter, a C-arm) directly to an affected part, comprises: a line laser module configured to generate a line laser to form a plane by rotating around an origin; a matching unit configured to calculate a coordinate representing the insertion location in a C-arm coordinate system based on the C-arm, calculate an insertional vector according to the coordinate representing the insertion location and the insertion angle, and calculate a vector perpendicular to the plane formed by the line laser in the C-arm coordinate system according to the insertional vector; and a control unit configured to control the line laser module based on the vector perpendicular to the plane formed by the line laser.

Meanwhile, the matching unit may be configured to calculate a coordinate representing the origin in the C-arm coordinate system, and calculate the vector perpendicular to the plane formed by the line laser by performing vector product to a vector connecting the coordinate representing the insertion location and the coordinate representing the origin and the insertional vector.

In addition, the matching unit may be configured to transform the vector perpendicular to the plane formed by the line laser in the C-arm coordinate system into a line laser module coordinate system based on the line laser module.

In addition, the matching unit may be configured to calculate an extrinsic parameter of a C-arm marker located at the line laser module in the C-arm image, derive a transformation matrix between the C-arm coordinate system and a C-arm marker coordinate system based on the C-arm marker, derive a transformation matrix between the C-arm marker coordinate system and a line laser module coordinate system based on the line laser module, and derive a transformation matrix between the C-arm coordinate system and the line laser module coordinate system.

In addition, the line laser module may include: a green laser configured to generate a laser beam; a rotation line generator configured to transform the laser beam into a line laser rotating around the origin; a rotating mirror configured to change a rotation central axis of the line laser; a first motor connected to the rotation line generator to operate under the control of the control unit; and a second motor connected to the rotating mirror to operate under the control of the control unit.

In addition, the control unit may be configured to control the first motor and the second motor by calculating steering angles of the first motor and the second motor, respectively, from the vector perpendicular to the plane formed by the line laser.

In addition, the line laser module may further include a calibration tool to which a calibration pattern is attached, and the calibration tool may be located between the line laser module and the C-arm.

Meanwhile, a control method of a laser projection apparatus according to another aspect of the present disclosure, which projects operation information of an insertion location and an insertion angle planned on a C-arm image photographed using a C-arm fluoroscopy (hereinafter, a C-arm) directly to an affected part, comprises: calculating a coordinate representing the insertion location in a C-arm coordinate system based on the C-arm; calculating an insertional vector according to the coordinate representing the insertion location and the insertion angle; calculating a vector perpendicular to a plane formed by a line laser generated by the laser projection apparatus in the C-arm coordinate system according to the insertional vector; and controlling the line laser to be generated based on the vector perpendicular to the plane formed by the line laser.

Meanwhile, said step of calculating a vector perpendicular to a plane formed by a line laser generated by the laser projection apparatus in the C-arm coordinate system according to the insertional vector may include calculating a coordinate representing an origin for rotation of the line laser in the C-arm coordinate system, and calculating the vector perpendicular to the plane formed by the line laser by performing vector product to a vector connecting the coordinate representing the insertion location and the coordinate representing the origin and the insertional vector.

In addition, the control method may further comprise transforming the vector perpendicular to the plane formed by the line laser in the C-arm coordinate system into a line laser module coordinate system based on the line laser module.

In addition, the control method may further comprise calculating an extrinsic parameter of a C-arm marker located at the line laser module in the C-arm image, deriving a transformation matrix between the C-arm coordinate system and a C-arm marker coordinate system based on the C-arm marker, deriving a transformation matrix between the C-arm marker coordinate system and a line laser module coordinate system based on the line laser module, and deriving a transformation matrix between the C-arm coordinate system and the line laser module coordinate system.

In addition, the line laser module may include: a green laser configured to generate a laser beam; a rotation line generator configured to transform the laser beam into a line laser rotating around an origin; a rotating mirror configured to change a rotation central axis of the line laser; a first motor connected to the rotation line generator to operate under the control of the control unit; and a second motor connected to the rotating mirror to operate under the control of the control unit, and said step of controlling the line laser to be generated based on the vector perpendicular to the plane formed by the line laser may include controlling the first motor and the second motor.

In addition, said step of controlling the line laser to be generated based on the vector perpendicular to the plane formed by the line laser may include controlling the first motor and the second motor by calculating steering angles of the first motor and the second motor, respectively, from the vector perpendicular to the plane formed by the line laser.

Meanwhile, a laser guidance system according to another aspect of the present disclosure comprises: a C-arm fluoroscopy (hereinafter, a C-arm); a display device configured to display an image photographed using the C-arm and receive operation information of an insertion location and an insertion angle from a user; and at least two laser projection apparatuses configured to project the operation information directly to an affected part, wherein the laser projection apparatus may include: a line laser module configured to generate a line laser to form a plane by rotating around an origin; a matching unit configured to calculate a coordinate representing the insertion location in a C-arm coordinate system based on the C-arm, calculate an insertional vector according to the coordinate representing the insertion location and the insertion angle, and calculate a vector perpendicular to the plane formed by the line laser in the C-arm coordinate system according to the insertional vector; and a control unit configured to control the line laser module based on the vector perpendicular to the plane formed by the line laser.

Meanwhile, the operation information may be displayed as an intersection point of line lasers generated from the at least two laser projection apparatuses.

In addition, the matching unit may be configured to calculate a coordinate representing the origin in the C-arm coordinate system, and calculate the vector perpendicular to the plane formed by the line laser by performing vector product to a vector connecting the coordinate representing the insertion location and the coordinate representing the origin and the insertional vector.

In addition, the line laser module may include: a green laser configured to generate a laser beam; a rotation line generator configured to transform the laser beam into a line laser rotating around the origin; a rotating mirror configured to change a rotation central axis of the line laser; a first motor connected to the rotation line generator to operate under the control of the control unit; and a second motor connected to the rotating mirror to operate under the control of the control unit.

In addition, the control unit may be configured to control the first motor and the second motor by calculating steering angles of the first motor and the second motor, respectively, from the vector perpendicular to the plane formed by the line laser.

In addition, the line laser module may further include a calibration tool located between the line laser module and the C-arm so that a calibration pattern is attached thereto.

In addition, the display device may include: a panel configured to display an image photographed using the C-arm; and an interface unit configured to provide a user interface allowing a touch input of a user to the panel and detect a touch input applied by the user.

Advantageous Effects

According to the present disclosure, since the operation information of the insertion location and the insertion angle planned on the C-arm image is directly displayed on the affected part as an intersection point of two line lasers, it is possible to help a the user (for example, a doctor) to precisely and easily perform a surgical operation.

BEST MODE

Figure 1:
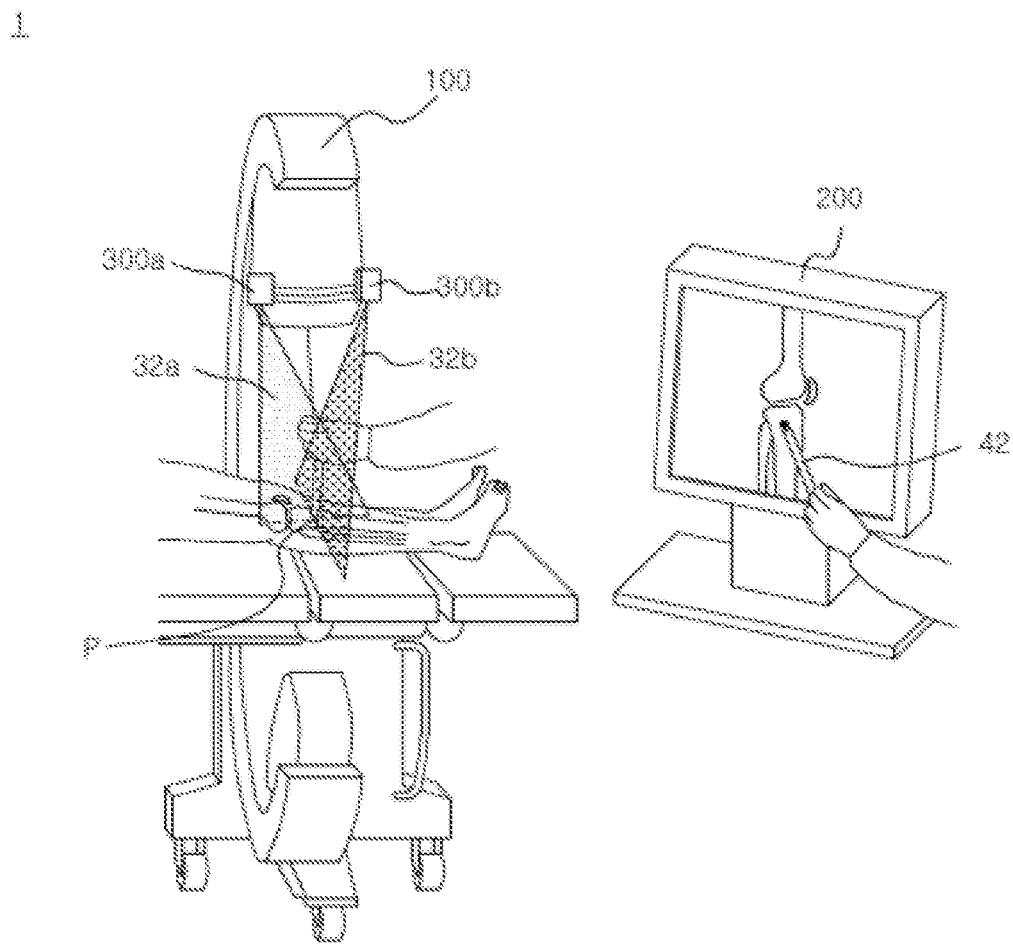
FIG. 1 is a diagram showing a laser guidance system according to an embodiment of the present disclosure.

The present disclosure will be described in detail with reference to the accompanying drawings which illustrate, by way of example, specific embodiments in which the present disclosure may be implemented. These embodiments are described in sufficient detail to enable those skilled in the art to implement the present disclosure. It should be understood that various embodiments of the present disclosure are different from each other but need not be mutually exclusive. For example, specific features, structures and characteristics described herein may be implemented in other embodiments without departing from the scope of the present disclosure in connection with one embodiment. It should also be understood that the position or arrangement of individual components in each embodiment may be varied without departing from the scope of the present disclosure. Therefore, the following detailed description is not taken to limit the present disclosure, and the scope of the present disclosure is limited only by the appended claims, along with the full scope of equivalents to which such claims are entitled. In the drawings, like reference signs refer to the same or similar functions throughout several aspects.

Hereinafter, preferred embodiments of the present disclosure will be described in more detail with reference to the drawings.

FIG. 1 is a diagram showing a laser guidance system according to an embodiment of the present disclosure.

Referring to FIG. 1, a laser guidance system 1 according to an embodiment of the present disclosure guides an insertion location and posture of a fixing screw, a drill, a guide, or the like in a surgical operation to help a user (for example, a doctor) to precisely and easily perform the surgical operation.

To this end, the laser guidance system 1 according to an embodiment of the present disclosure includes a C-arm fluoroscopy (hereinafter, a C-arm) 100, a display device 200 and laser projection apparatuses 300a, 300b, and may display operation information of an insertion location and an insertion angle planned on a C-arm image photographed using the C-arm 100 directly displayed on an affected part as an intersection point P of two line lasers 32a, 32b.

Specifically, the C-arm 100 is a device that scans the human body and photographs a surgical site, and a C-arm image, which is an image photographed by the C-arm, may be a 2D C-arm fluoroscopic image. The C-arm 100 may transmit the photographed image to the display device 200.

The display device 200 may output the C-arm image and receive operation information from a user. To this end, the display device 200 may include a display panel displaying the C-arm image and an interface unit that provides a user interface (UI) for allowing a user to apply a touch input and senses a touch input applied by the user. That is, the display device 200 provides a function for a user to graphically display and change operation information directly on the C-arm image, and thus the display panel may include a touch screen function or a separate touch pad. For example, if the display device 200 is configured as a display panel having a touch screen function as shown in FIG. 1, the user may plan the operation information on the C-arm image displayed on the display panel by using an electrical pen 42 or by hand.

The laser projection apparatuses 300a, 300b are devices that generate a line laser and projects the line laser on an affected part according to the operation information planned on the C-arm image, and the laser projection apparatuses 300a, 300b may be coupled to the C-arm 100 as shown in FIG. 1. The laser projection apparatuses 300a, 300b may perform position matching between the C-arm 100 and the laser projection apparatuses 300a, 300b in order to project line lasers at a position according to the operation information planned on the C-arm image. As described above, the laser guidance system 1 according to an embodiment of the present disclosure may display the operation information on the affected part as an intersection point P of two line lasers 32a, 32b. Therefore, at least two laser projection apparatuses 300a, 300b may be provided. The laser projection apparatuses 300a, 300b will be described in more detail with reference to FIGS. 2 to 9.

Figure 2:
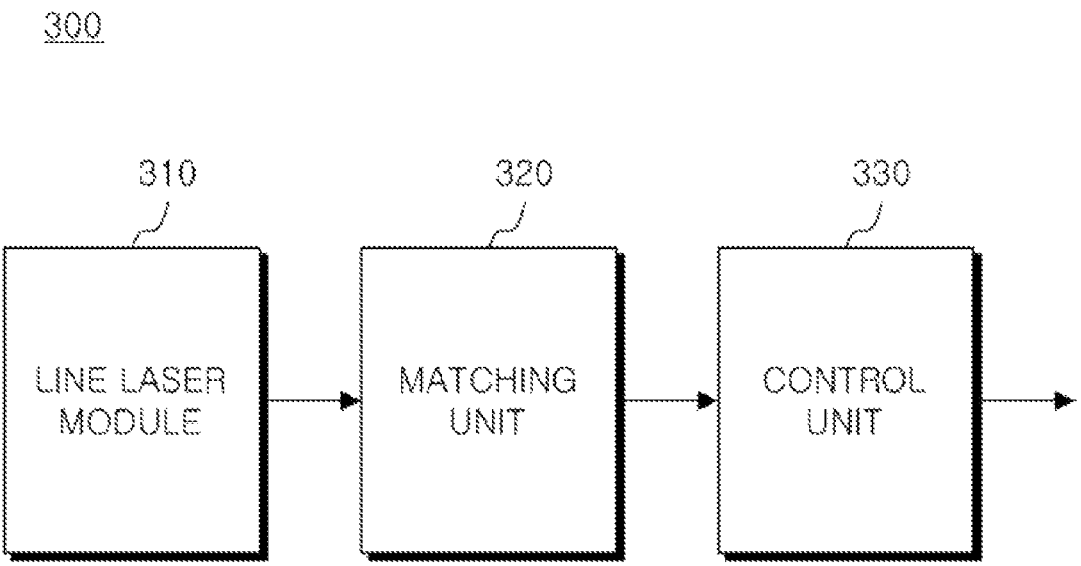
FIG. 2 is a control block diagram showing the laser projection apparatus of FIG. 1.

FIG. 2 is a control block diagram showing the laser projection apparatus of FIG. 1.

Referring to FIG. 2, the laser projection apparatus 300 may include a line laser module 310 for generating a line laser, a matching unit 320 for performing position matching between the C-arm 100 and the laser projection apparatus 300, and a control unit 330 for controlling the line laser module 310 according to the matching result. Hereinafter, each component of the laser projection apparatus 300 will be described in detail.

The line laser module 310 may generate a line laser. The configuration of the line laser module 310 for this function will be described with reference to FIG. 3.

Figure 3:
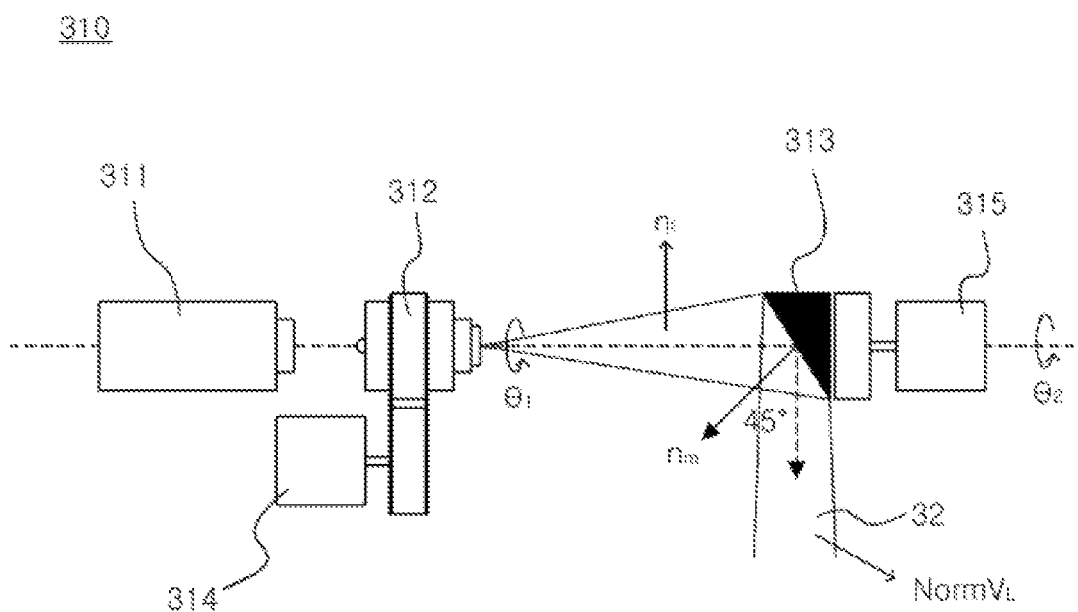
FIG. 3 is a diagram schematically showing a line laser module.

FIG. 3 is a diagram schematically showing a line laser module.

Referring to FIG. 3, the line laser module 310 may be implemented to include a green laser 311, a rotation line generator 312, a rotating mirror 313, a first motor 314 and a second motor 315, and these configurations may be accommodated in a housing that defines the appearance of the line laser module 310.

The green laser 311 may generate a laser beam. In this embodiment, the configuration for laser generation is defined as the green laser 311 that generates a green laser beam, but the color of the laser beam is not limited.

The rotation line generator 312 may transform the laser beam to the line laser 32 by rotating the laser beam around an origin. That is, the rotation line generator 312 may rotate the laser beam so that the laser beam consequently forms a plane and thus is transformed into the line laser 32 projected in a line form on the target. The rotation line generator 312 may receive two degree of freedom movement by the first motor 314. The rotation line generator 312 may rotate according to the operation of the first motor 314, so that the laser beam is rotated around the origin and transformed into the line laser 32. At this time, a rotation angle ($\theta_1$) of the line laser 32 may be a rotation angle ($\theta_1$) of the first motor 314, and its value may be calculated by the matching unit 320 and control unit 330, which is explained below.

The rotating mirror 313 may be located to face the rotation line generator 312 to reflect the line laser 32. The rotating mirror 313 may change the direction of a rotation central axis of line laser 32. If the direction of the rotation central axis of the line laser 32 is changed, the direction ($n_l$) of the plane formed by the line laser 32 may be changed. Two degree of freedom movement of the rotating mirror 313 may be supported by the second motor 315. The rotating mirror 313 may change a direction ($n_m$) of the rotating mirror 313 according to the operation of the second motor 315. The rotating mirror 313 may reflect the line laser 32 at an angle of 45° with respect to the direction ($n_m$) of the rotating mirror 313. As a result, the line laser 32 may be projected on a target according to the direction ($n_m$) of the rotating mirror 313. The direction ($n_m$) of the rotating mirror 313 may be determined according to a rotation angle ($\theta_2$) of the second motor 315, and the rotation angle ($\theta_2$) may be calculated by the matching unit 320 and control unit 330, explained later.

The first motor 314 and the second motor 315 may have two degree of freedom steering. The first motor 314 and the second motor 315 may operate under control of the control unit 330. The first motor 314 may be connected to the rotation line generator 312 to provide two degree of freedom movement to the rotation line generator 312. The second motor 315 may be connected to the rotating mirror 313 to provide two degree of freedom movement to the rotating mirror 313. The rotation angles ($\theta_1$, $\theta_2$) of the first motor 314 and the second motor 315 may be calculated from a vector ($_{Norm}V_L$) perpendicular to the plane formed by the line laser 32 projected to the affected part, respectively. This will be described later in detail.

Meanwhile, as described above, the laser projection apparatus 300 performs position matching between the C-arm 100 and the laser projection apparatus 300. To this end, the line laser module 310 may further include a calibration tool 336, and a C-arm marker appearing on the C-arm image may be attached to a predetermined position of the calibration tool 336 so as to check the position of the line laser module 310 based on the C-arm 100.

Figure 4:
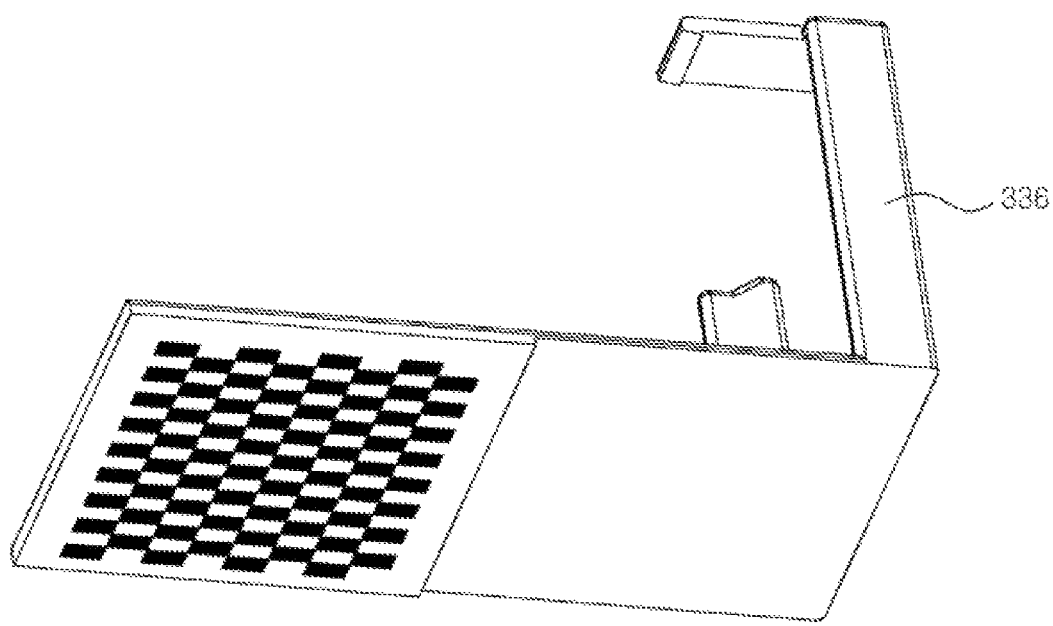
FIG. 4 shows an example of a calibration tool included in the line laser module.

FIG. 4 shows an example of a calibration tool included in the line laser module.

Referring to FIG. 4, the calibration tool 336 may have a checkerboard-shaped calibration pattern attached to a lower surface thereof. The calibration tool 336 may be mounted to the line laser module 310 to be located between the line laser module 310 and the C-arm 100. Therefore, the line laser 32 may be projected to the affected part through the calibration tool 336, and the calibration pattern may be projected on the C-arm image.

The matching unit 320 performs calculation for position matching between the C-arm 100 and the laser projection apparatus 300, and may calculate a vertical vector ($_{Norm}V_L$) that is perpendicular to the plane formed by the line laser 32 in order to calculate the rotation angles ($\theta_1$, $\theta_2$) of the first motor 314 and the second motor 315, respectively.

First, referring to FIGS. 5 to 7, coordinate systems used in the matching unit 320 for position matching between the C-arm and the laser projection apparatus will be described.

Figure 5:
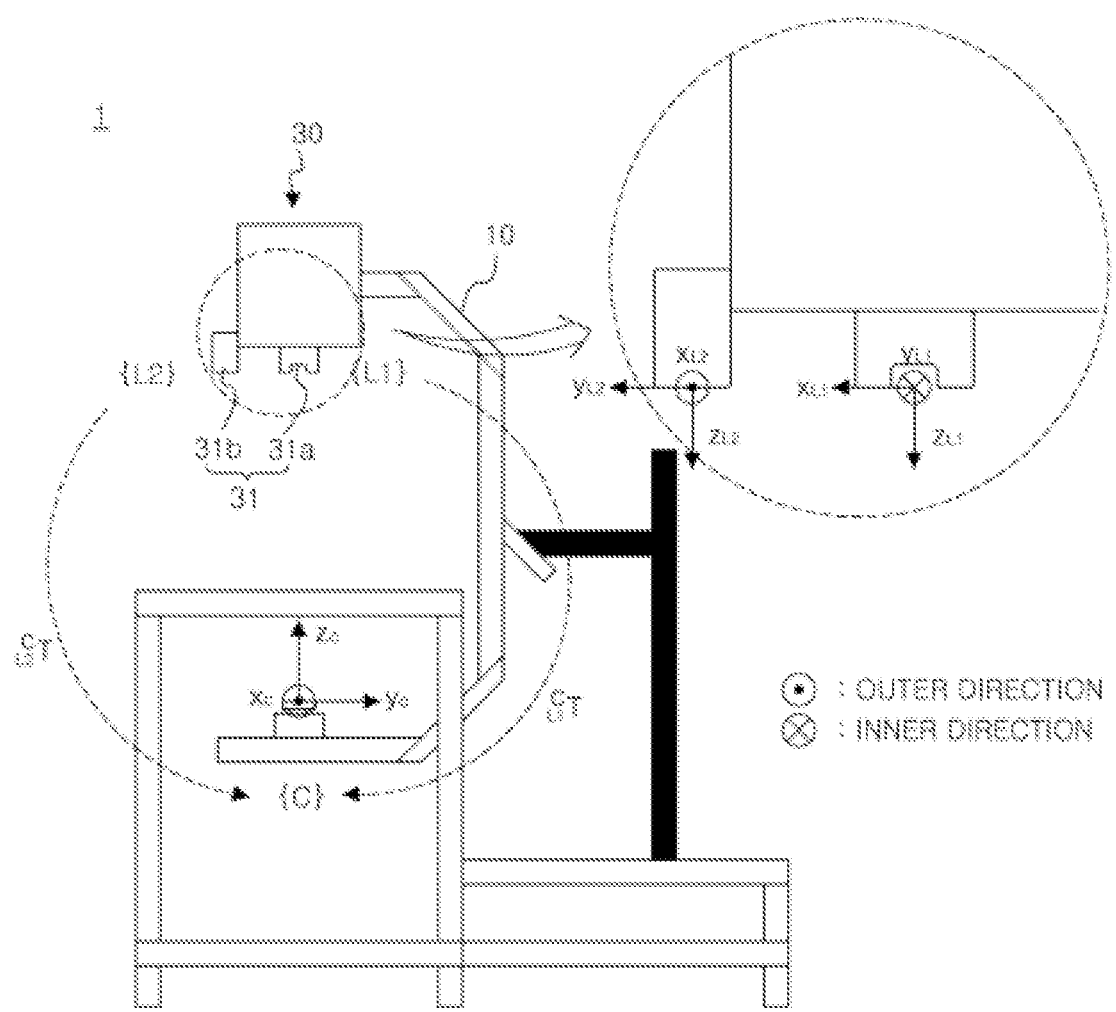
FIGS. 5 to 7 are diagrams for illustrating coordinate systems used for matching positions of a C-arm and a laser projection apparatus.
Figure 6:
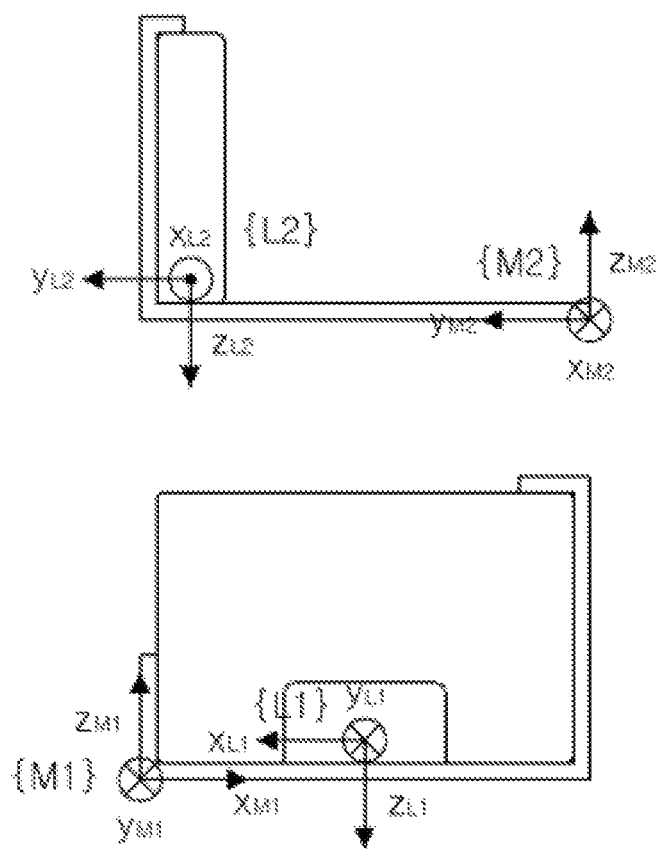
Figure 7:
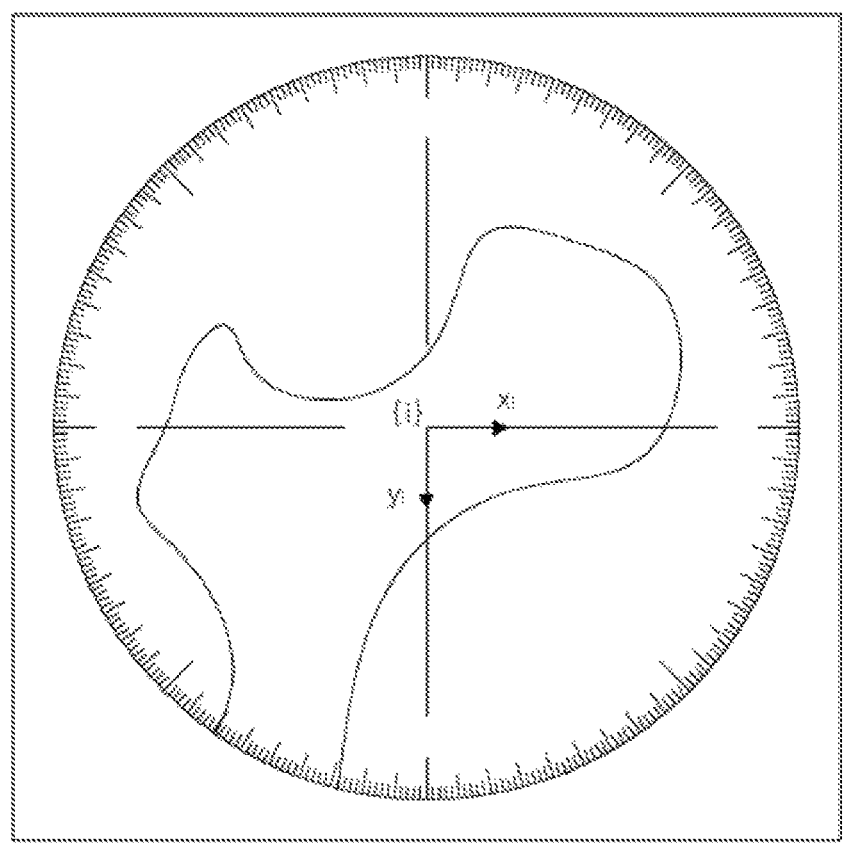

FIGS. 5 to 7 are diagrams for illustrating coordinate systems used for matching positions of a C-arm and a laser projection apparatus.

Referring to FIG. 5, {C} represents a C-arm coordinate system based on the C-arm 100. {L1} and {L2} represent line laser module coordinate systems based on a first laser projection apparatus 31a and a second laser projection apparatus 31b, respectively, and more specifically, they are coordinate systems based on the origin of the line laser output from the line laser module 310 included in each laser projection apparatus 300.

Referring to FIG. 6, {M1} and {M2} represent C-arm marker coordinate systems based on C-arm markers attached to the first laser projection apparatus 31a and the second laser projection apparatus 31b, respectively. The matching unit 320 may derive a transformation matrix $_M^LT$ between {M} and {L} and may also derive a transformation matrix $_C^MT$ between {C} and {M}. The matching unit 320 may derive a transformation matrix $_C^LT$ between {L} and {C} by using $_M^LT$ and $_C^MT$, and may express the coordinate of {L1} or {L2} as a coordinate of {C} by using this transformation matrix.

Referring to FIG. 7, {i} represents a C-arm image coordinate system based on the C-arm image, which is a bi-axis coordinate system, unlike the tri-axial coordinate systems {C}, {L}, {M}. The matching unit 320 may calculate the coordinate of {i} in {C}.

Hereinafter, the calculation for position matching between the C-arm 100 and the laser projection apparatus 300 by the matching unit 320 will be described.

In order to derive a transformation matrix $_C^LT$ between {C} and {L}, the matching unit 320 may first derive a transformation matrix $_C^MT$ between {C} and {L}. The matching unit 320 may derive the transformation matrix $_C^MT$ between {C} and {L} using the known Zhang's camera calibration method. As described above, a C-arm marker may be attached to the laser projection apparatus 300, and the C-arm marker may appear on the C-arm image. The matching unit 320 may calculate an extrinsic parameter of the C-arm marker using the Zhang's camera calibration method on the C-arm image. At this time, the matching unit 320 may calculate the extrinsic parameter of the C-arm marker based on a calibration pattern projected on the C-arm image. The specifications of the calibration tool 336 and the design information of the calibration pattern thereof may be stored in advance. The matching unit 320 may derive the transformation matrix $_C^MT$ between {C} and {L} according to the extrinsic parameter of the C-arm marker, and may transform any one coordinate of {C} into a coordinate value of {M} by using the transformation matrix $_C^MT$.

In addition, the matching unit 320 may derive a transformation matrix $_M^LT$ between {M} and {L}. As shown in FIG. 6, the coordinate system {L} based on the origin of the line laser output from the line laser module 310 is the same as a coordinate system obtained by rotating the coordinate system {M} by 180° about the y-axis of based on the C-arm marker. Therefore, the matching unit 320 may derive the transformation matrix $_M^LT$ between {M} and {L} as in Equation 1 below, and transform any one coordinate of {M} to the coordinate value of {L} using the transformation matrix $_M^LT$.

$$^L_MT = \begin{bmatrix} -1 & 0 & 0 & x \\ 0 & 1 & 0 & y \\ 0 & 0 & -1 & z \\ 0 & 0 & 0 & 1 \end{bmatrix} \quad \text{[Equation 1]}$$

In Equation 1, x, y and z are determined according to the design of the calibration tool 336, and may be determined according to a distance between the origin of the line laser output from the line laser module 310 and the origin of the calibration pattern.

The matching unit 320 may derive the transformation matrix $_C^LT$ between {C} and {L} using $_C^MT$ and $_M^LT$ derived as above. The matching unit 320 may derive a transformation matrix $_C^{L1}T$ between {C} and {L1} using $_C^{M1}T$ and $_{M1}^{L1}T$ as in Equation 2 below, and may transform any one coordinate of {C} into a coordinate value of {L1} using the transformation matrix $_C^{L1}T$. In addition, the matching unit 320 may derive a transformation matrix $_C^{L2}T$ between {C} and {L2} using $_C^{M2}T$ and $_{M2}^{L2}T$ as in Equation 3 below, and may transform any one coordinate of {C} into a coordinate value of {L2} using the transformation matrix $_C^{L2}T$.

$$_C^{L1}T = {}_{M1}^{L1}T\, _C^{M1}T = {}_{L1}^{M1}T\, _C^{-1M1}T \quad \text{[Equation 2]}$$

$$_C^{L2}T = {}_{M2}^{L2}T\, _C^{M2}T = {}_{L2}^{M2}T\, _C^{-1M2}T \quad \text{[Equation 3]}$$

Meanwhile, the matching unit 320 may transform one point $P_{img}$ (x, y) of {i} into one point P ($X_c$, $Y_c$, $Z_c$) of {C}. Here, $P_{img}$ (x, y) may be an insertion location displayed on the C-arm image by the user. The matching unit 320 may transform {i} into a normal coordinate system, and then transform into {C} in the normal coordinate system. This will be described with reference to FIG. 8.

Figure 8:
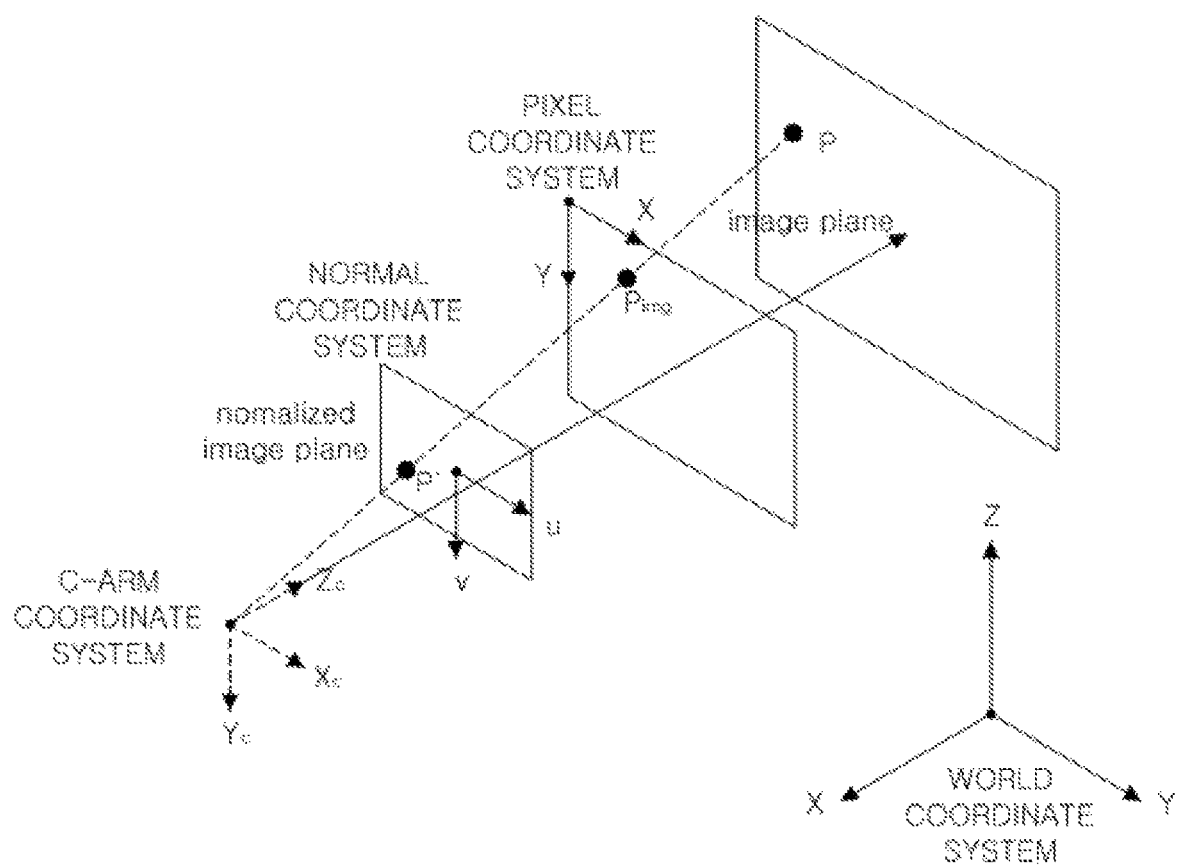
FIG. 8 is a diagram for illustrating a method of displaying a point of a C-arm image coordinate system based on a C-arm image as a point of a C-arm coordinate system based on the C-arm.

FIG. 8 is a diagram for illustrating a method of displaying a point of a C-arm image coordinate system based on a C-arm image as a point of a C-arm coordinate system based on the C-arm.

The matching unit 320 may obtain an intrinsic parameter k of the C-arm as in Equation 4 using the known Zhang's method, and may obtain a parameter for transforming {i} into a normal coordinate system as in Equations 5 and 6 below.

$$K = \begin{bmatrix} fx & 0 & cx \\ 0 & fy & cy \\ 0 & 0 & 1 \end{bmatrix} \quad \text{[Equation 4]}$$

$$\begin{bmatrix} x \\ y \\ 1 \end{bmatrix} = \begin{bmatrix} fx & 0 & cx \\ 0 & fy & cy \\ 0 & 0 & 1 \end{bmatrix} \begin{bmatrix} u \\ v \\ 1 \end{bmatrix} \quad \text{[Equation 5]}$$

$$u = \frac{x-cx}{fx}, v = \frac{y-cx}{fy} \quad \text{[Equation 6]}$$

The matching unit 320 may transform the normal coordinate system into {C}. The C-arm image is a plane parallel to the intensifier of the C-arm 100, and the distance between the C-arm 100 and a photographing target may checked in advance. For example, if the distance from the origin of {C} to the photographing target is d, P ($X_c$, $Y_c$, $Z_c$) may be calculated as in Equation 7 below.

$$X_C = u \times d, Y_C = v \times d, Z_C = d \quad \text{[Equation 7]}$$

If the coordinate P ($X_c$, $Y_c$, $Z_c$) representing the insertion location in {C} is calculated, the matching unit 320 may calculate an insertional vector according to the insertion angle received from the user. In addition, the matching unit 320 may calculate a coordinate representing the origin of the line laser module 310 in {C}. In addition, the matching unit 320 may calculate a vector ($_{Norm}V_L$) perpendicular to the plane formed by the line laser 32 according to the insertional vector and the coordinates representing the origin of the line laser module 310. This will be described with reference to FIG. 9.

Figure 9:
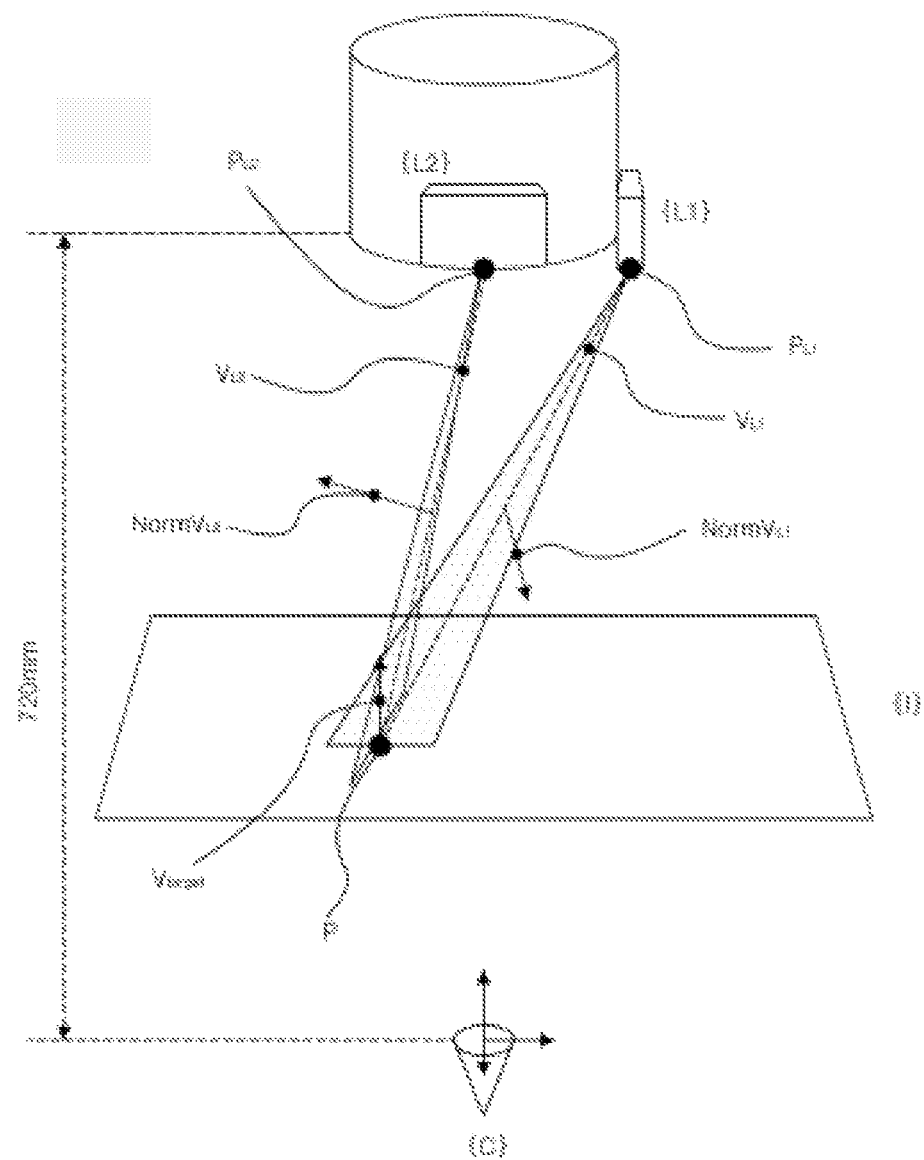
FIG. 9 is a diagram for illustrating a vector calculated by a matching unit depicted in FIG. 2.

FIG. 9 is a diagram for illustrating a vector calculated by a matching unit depicted in FIG. 2.

First, the matching unit 320 may calculate an insertional vector ($V_{target}$) according to the insertion angle (α) input by the user at the coordinate P ($X_c$, $Y_c$, $Z_c$) representing the insertion location in {C}.

In addition, the matching unit 320 may calculate the coordinates ($P_{L1}$, $P_{L2}$) representing the origin of the line laser module 310 in {C} by using the transformation matrix $_C^LT$ between {C} and {L} as in Equation 8 below.

$$P_{L1} = {}_{L1}^CT^{L1} P_{(0,0,0)}$$

$$P_{L2} = {}_{L2}^CT^{L2} P_{(0,0,0)} \quad \text{[Equation 8]}$$

In addition, the matching unit 320 may calculate a vector ($_{Norm}V_L$) perpendicular to the plane formed by the line laser 32 in {C} as in Equation 9 below. The matching unit 320 may calculate the vector ($_{Norm}V_L$) perpendicular to the plane formed by the line laser 32 by performing vector product a vector connecting the coordinate representing the origin of the line laser module 310 in {C} and the coordinate representing the insertion location and the insertional vector.

$$_{Norm}V_{L1} = V_{target} \times \overrightarrow{PP_{L1}}$$

$$_{Norm}V_{L1} = V_{target} \times \overrightarrow{PP_{L2}} \quad \text{[Equation 9]}$$

Since the vector ($_{Norm}V_L$) perpendicular to the plane formed by the line laser 32 according to Equation 9 is a vector based on {C}, the matching unit 320 may transform the vector ($_{Norm}V_L$) into a vector based on {L}, and the resulting vector of the line laser 32 may be expressed as in Equation 10 below.

$$V_{L1} = {}^{L1}_C R_{Norm} V_{L1}, V_{L2} = {}^{L2}_C R_{Norm} V_{L2} \quad \text{[Equation 10]}$$

The control unit 330 may control the line laser module 310 based on the vector ($_{Norm}V_L$) perpendicular to the plane formed by the line laser 32 so that the line laser 32 according to Equation 10 may be projected onto the affected part. That is, the control unit 330 may control the first motor 314 and the second motor 315 by calculating the steering angles of the first motor 314 and the second motor 315 of the line laser module 310, respectively. In the following description, the steering angle of the first motor 314 is referred to as a first rotation angle ($\theta_1$), and the steering angle of the second motor 315 is referred to as a second rotation angle ($\theta_2$).

Specifically, as shown in FIG. 3, the vector ($_{Norm}V_L$) perpendicular to the plane formed by the line laser 32 may be expressed as in Equation 11 below.

$$\text{Norm}V_L = n_l - 2(n_l \cdot n_m)_m \quad \text{[Equation 11]}$$

In Equation 11, $n_1$ may represent a direction facing the plane formed by the line laser 32, and $n_m$ may represent a direction of the rotating mirror 313.

In Equation 11 $n_1$, $n_m$ and $n_1 \cdot n_m$ may be expressed as in Equation 12 below by using the first rotation angle ($\theta_1$) and the second rotation angle ($\theta_2$).

$$n_l = [0 \;\; \cos\theta_1 \;\; \sin\theta_2], \quad \text{[Equation 12]}$$

$$n_m = \left[-\frac{\sqrt{2}}{2} \;\; -\frac{\sqrt{2}}{2}\sin\theta_2 \;\; \frac{\sqrt{2}}{2}\cos\theta_2\right],$$

$$n_l \cdot n_m = \frac{\sin(\theta_1 - \theta_2)}{\sqrt{2}}$$

If Equation 12 is applied to Equation 11, the vector $(_{Norm}V_L)$ (perpendicular to the plane formed by the line laser 32 may be expressed as in Equation 13 below.

$$\text{Norm}V_L = [\sin(\theta_1-\theta_2)\cos(\theta_1-\theta_2)\cos\theta_2 \;\; \cos(\theta_1-\theta_2)\sin\theta_2] \quad \text{[Equation 13]}$$

Accordingly, the control unit 330 may calculate the first rotation angle ($\theta_1$) and the second rotation angle ($\theta_2$), respectively, based on Equation 13. For example, the control unit 330 may calculate $\theta_1-\theta_2$ by comparing the x value of the vector $(_{Norm}V_L)$ perpendicular to the plane formed by the line laser 32 with $\sin(\theta_1-\theta_2)$, calculate second rotation angle ($\theta_2$) by applying the calculated $\theta_1-\theta_2$ value to the y and z values of the vector $(_{Norm}V_L)$ perpendicular to the plane formed by the line laser 32 first, and then calculate the first rotation angle ($\theta_1$).

The control unit 330 may control the first motor 314 and the second motor 315 according to the first rotation angle ($\theta_1$) and the second rotation angle ($\theta_2$) calculated as above.

Hereinafter, referring to FIG. 10, a control method of the laser projection apparatus according to an embodiment of the present disclosure as shown in FIG. 2 will be described.

Figure 10:
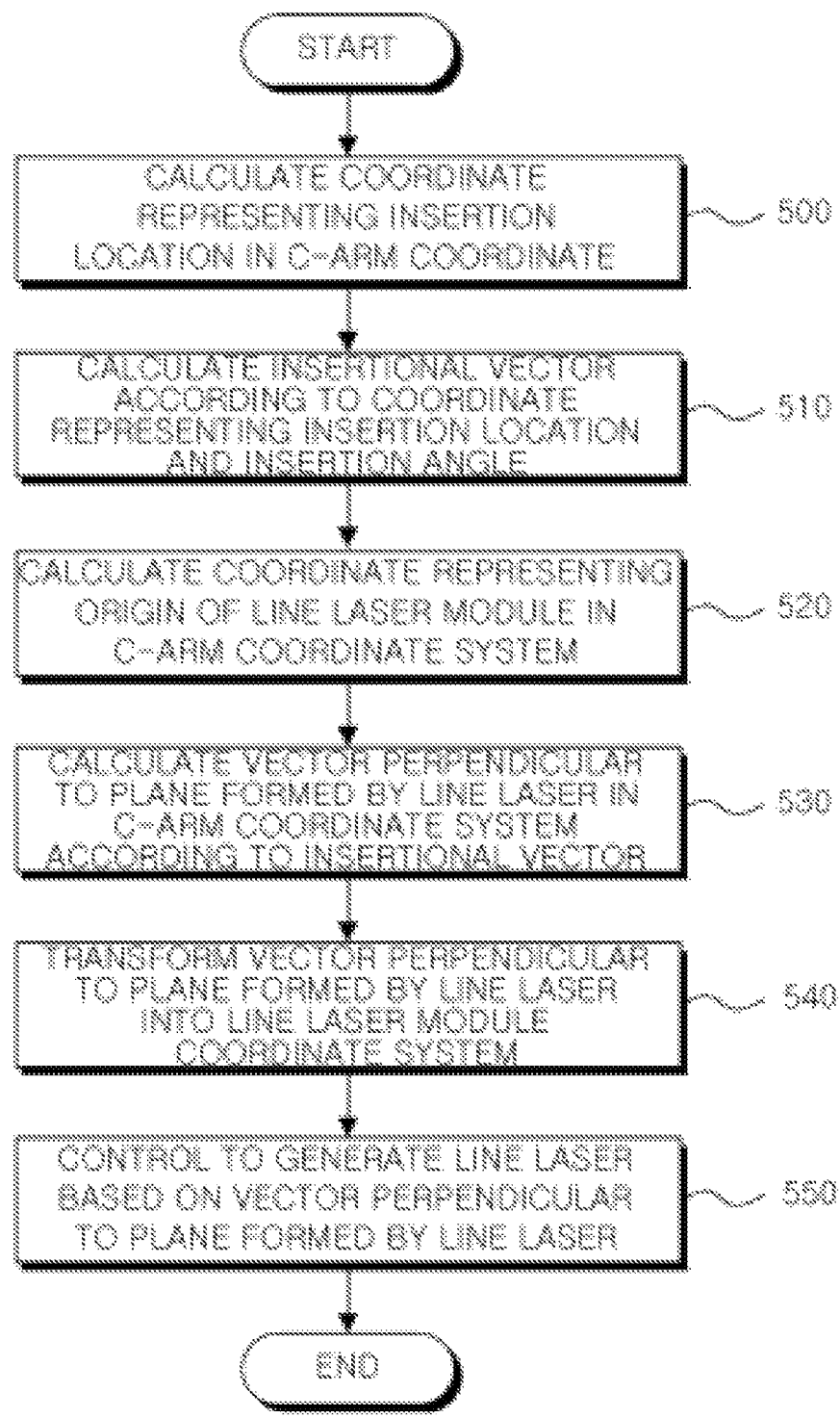
FIG. 10 is a flowchart for illustrating a control method of the laser projection apparatus according to an embodiment of the present disclosure as shown in FIG. 2.

FIG. 10 is a flowchart for illustrating a control method of the laser projection apparatus according to an embodiment of the present disclosure as shown in FIG. 2.

Referring to FIG. 10, the laser projection apparatus 300 may calculate a coordinate representing the insertion location in the C-arm coordinate system (500). The laser projection apparatus 300 may transform $P_{img}$ (x, y), which is an insertion location displayed on the C-arm image by the user in {i}, into a point P ($X_c$, $Y_c$, $Z_c$) of {C} according to Equations 4 to 7. The laser projection apparatus 300 may transform {i} into a normal coordinate system, and then transform into {C} in the normal coordinate system.

In addition, the laser projection apparatus 300 may calculate an insertional vector according to the coordinate representing the insertion location and the insertion angle (510). The laser projection apparatus 300 may calculate the insertional vector ($V_{target}$) according to the insertion angle ($\alpha$) input by the user at the coordinate P ($X_c$, $Y_c$, $Z_c$) indicating the insertion location in {C}.

In addition, the laser projection apparatus 300 may calculate the coordinate ($P_{L1}$, $P_{L2}$) representing the origin of the line laser module 310 in the C-arm coordinate system (520). The laser projection apparatus 300 may calculate the coordinate ($P_{L1}$, $P_{L2}$) representing the origin of the line laser module 310 in {C} using the transformation matrix $^L_C T$ between {C} and {L}, as in Equation 8.

In addition, the laser projection apparatus 300 may calculate a vector $(_{Norm}V_L)$ perpendicular to the plane formed by the line laser 32 in the C-arm coordinate system according to the insertional vector (530). The laser projection apparatus 300 may calculate vector $(_{Norm}V_L)$ perpendicular to the plane formed by the line laser 32 by performing vector product to a vector connecting the coordinate representing the origin of the line laser module 310 in {C} and the coordinate representing the insertion location and the insertional vector, as in Equation 9.

In addition, the laser projection apparatus 300 may transform the vector $(_{Norm}V_L)$ perpendicular to the plane formed by line laser 32 in the C-arm coordinate system into a line laser module coordinate system (540). The laser projection apparatus 300 may transform the vector $(_{Norm}V_L)$ perpendicular to the plane formed by the line laser 32 based on {C} into a vector based on {L}, as in Equation 10.

In addition, the laser projection apparatus 300 may control to generate the line laser 32 based on the vector $(_{Norm}V_L)$ perpendicular to the plane formed by the line laser 32 (550). The laser projection apparatus 300 may control the first motor 314 and the second motor 315 by calculating the first rotation angle ($\theta_1$) of the first motor 314 connected to the rotation line generator 312 that converts the laser beam into the line laser 32 based on Equation 13 and calculating the second rotation angle ($\theta_2$) of the second motor 315 connected to the rotating mirror 313 that converts the rotation central axis of the line laser 32.

The control method of laser projection apparatus may be implemented in the form of an application or program commands executable by various computer components and be recorded on a computer-readable recording medium. The computer-readable recording medium may include program commands, data files, data structures or the like solely or in combination.

The program commands recorded on the computer-readable recording medium may be specially designed or configured for the present disclosure or known to and available by computer software engineers.

The computer-readable recording medium includes, for example, magnetic media such as a hard disk, a floppy disk and a magnetic tape, optical media such as CD-ROM and DVD, magneto-optical media such as a floptical disk, hardware devices such as ROM, RAM and a flash memory, specially configured to store and perform program commands, or the like.

The program commands include not only machine codes made by a complier but also high-level language codes executable by a computer by using an interpreter. The hardware device may be configured to operate as at least one software module to perform the operations of the present disclosure, or vice versa.

While the present disclosure has been described with reference to the embodiments, it will be understood by those skilled in the art that various changes and modifications can be made without departing from the scope of the present disclosure as set forth in the appended claims.

The invention claimed is:

1. A laser projection apparatus for projecting planned operation information of an insertion location and an insertion angle on a C-arm image photographed using a C-arm fluoroscopy device directly onto an affected part, the laser projection apparatus comprising:
   a line laser module configured to generate a line laser and to form a plane by rotating around an origin;
   a matching unit configured to calculate a coordinate representing the insertion location in a C-arm coordinate system based on C-arm fluoroscopy, calculate an insertional vector according to the coordinate representing the insertion location and the insertion angle, and calculate a vector perpendicular to the plane formed by the line laser in the C-arm coordinate system according to the insertional vector; and
   a control unit configured to control the line laser module based on the vector perpendicular to the plane.

2. The laser projection apparatus of claim 1,
wherein the matching unit is further configured to calculate a coordinate representing the origin in the C-arm coordinate system, and calculate the vector perpendicular to the plane by performing vector product between a vector connecting the coordinate representing the insertion location and the coordinate representing the origin and the insertional vector.

3. The laser projection apparatus of claim 2,
wherein the matching unit is further configured to transform the vector perpendicular to the plane in the C-arm coordinate system into a line laser module coordinate system, the line laser module coordinate system being based on the line laser module.

4. The laser projection apparatus of claim 1,
wherein the matching unit is further configured to calculate in the C-arm image an extrinsic parameter of a C-arm marker located at the line laser module, derive a transformation matrix between the C-arm coordinate system and a C-arm marker coordinate system based on the C-arm marker, derive a transformation matrix between the C-arm marker coordinate system and a line laser module coordinate system based on the line laser module, and derive a transformation matrix between the C-arm coordinate system and the line laser module coordinate system.

5. The laser projection apparatus of claim 1,
wherein the line laser module comprises:
a green laser configured to generate a laser beam;
a rotation line generator configured to transform the laser beam into the line laser by rotating the laser beam around the origin;
a rotating mirror configured to change a central rotation axis of the line laser;
a first motor connected to the rotation line generator and configured to operate under the control of the control unit; and
a second motor connected to the rotating mirror and configured to operate under the control of the control unit.

6. The laser projection apparatus of claim 5,
wherein the control unit is further configured to control the first motor and the second motor by calculating steering angles of the first motor and the second motor, respectively, from the vector perpendicular to the plane.

7. The laser projection apparatus of claim 5,
wherein the line laser module further comprises a calibration tool having a calibration pattern attached thereto, and
wherein the calibration tool is disposed between the line laser module and the C-arm fluoroscopy device.

8. A control method of a laser projection apparatus for projecting planned operation information of an insertion location and an insertion angle on a C-arm image photographed using a C-arm fluoroscopy device directly onto an affected part, the control method comprising:
calculating a coordinate representing the insertion location in a C-arm coordinate system based on C-arm fluoroscopy;
calculating an insertional vector according to the coordinate representing the insertion location and the insertion angle;
calculating a vector perpendicular to a plane formed by a line laser generated by the laser projection apparatus in the C-arm coordinate system according to the insertional vector; and
controlling the line laser to be generated based on the vector perpendicular to the plane.

9. The control method of claim 8,
wherein the calculating the vector perpendicular to the plane comprises:
calculating a coordinate representing an origin for rotation of the line laser in the C-arm coordinate system; and
calculating the vector perpendicular to the plane by performing vector product between a vector connecting the coordinate representing the insertion location and the coordinate representing the origin and the insertional vector.

10. The control method of claim 8, further comprising:
transforming the vector perpendicular to the plane in the C-arm coordinate system into a line laser module coordinate system.

11. The control method of claim 8, further comprising:
calculating an extrinsic parameter of a C-arm marker in the C-arm image, deriving a transformation matrix between the C-arm coordinate system and a C-arm marker coordinate system based on the C-arm marker, deriving a transformation matrix between the C-arm marker coordinate system and a line laser module coordinate system, and deriving a transformation matrix between the C-arm coordinate system and the line laser module coordinate system.

12. The control method of claim 8,
wherein the line laser is generated by a line laser module of the laser projection apparatus,
wherein the line laser module comprises:
a green laser configured to generate a laser beam;
a rotation line generator configured to transform the laser beam into the line laser by rotating the laser beam around an origin;
a rotating mirror configured to change a central rotation axis of the line laser;
a first motor connected to the rotation line generator; and
a second motor connected to the rotating mirror, and
wherein the controlling the line laser to be generated comprises controlling the first motor and the second motor.

13. The control method of claim 12,
wherein the controlling the line laser to be generated further comprises:
controlling the first motor and the second motor by calculating steering angles of the first motor and the second motor, respectively, from the vector perpendicular to the plane.

14. A laser guidance system comprising:
a C-arm fluoroscopy device;
a display device configured to display an image photographed using the C-arm fluoroscopy device and receive from a user operation information of an insertion location and an insertion angle; and
at least two laser projection apparatuses configured to project the operation information directly onto an affected part,
wherein each of the at least two laser projection apparatuses comprises:
a line laser module configured to generate a line laser and to form a plane by rotating around an origin;
a matching unit configured to calculate a coordinate representing the insertion location in a C-arm coordinate system based on C-arm fluoroscopy, calculate an insertional vector according to the coordinate representing the insertion location and the insertion angle, and calculate a vector perpendicular to the plane formed by the line laser in the C-arm coordinate system according to the insertional vector; and a control unit configured to control the line laser module based on the vector perpendicular to the plane.

15. The laser guidance system of claim 14,
wherein the operation information is displayed as an intersection point of line lasers generated from the at least two laser projection apparatuses.

16. The laser guidance system of claim 14,
wherein the matching unit is further configured to calculate a coordinate representing the origin in the C-arm coordinate system, and calculate the vector perpendicular to the plane by performing vector product between a vector connecting the coordinate representing the insertion location and the coordinate representing the origin and the insertional vector.

17. The laser guidance system of claim 14,
wherein the line laser module comprises:
a green laser configured to generate a laser beam;
a rotation line generator configured to transform the laser beam into the line laser by rotating the laser beam around the origin;
a rotating mirror configured to change a central rotation axis of the line laser;
a first motor connected to the rotation line generator and configured to operate under the control of the control unit; and
a second motor connected to the rotating mirror and configured to operate under the control of the control unit.

18. The laser guidance system of claim 17,
wherein the control unit is further configured to control the first motor and the second motor by calculating steering angles of the first motor and the second motor, respectively, from the vector perpendicular to the plane.

19. The laser guidance system of claim 17,
wherein the line laser module further comprises a calibration tool having a calibration pattern attached thereto, and
wherein the calibration tool is disposed between the line laser module and the C-arm fluoroscopy device.

20. The laser guidance system of claim 14,
wherein the display device comprises:
a panel configured to display the image photographed using the C-arm fluoroscopy device; and
a user interface provided in the panel and configured to detect a touch input applied by the user.

* * * * *